United States Patent [19]
Gross et al.

[11] Patent Number: 5,091,573
[45] Date of Patent: Feb. 25, 1992

[54] THIOL-TERMINATED HYDROXYAMIDES

[75] Inventors: Andrew W. Gross, Hatboro; William D. Emmons, Huntingdon Valley, both of Pa.

[73] Assignee: Rohm and Haas Company, Philadelphia, Pa.

[21] Appl. No.: 581,158

[22] Filed: Aug. 27, 1990

Related U.S. Application Data

[63] Continuation of Ser. No. 392,491, Aug. 11, 1990, abandoned.

[51] Int. Cl.$^5$ .................. C07C 323/60; C07C 233/20; C08F 2/38; C08G 63/685
[52] U.S. Cl. .................................. 564/192; 526/211; 528/364; 564/160
[58] Field of Search ...................... 564/192, 154, 160; 526/211; 528/364

[56] References Cited

U.S. PATENT DOCUMENTS

| | | | |
|---|---|---|---|
| 3,093,146 | 6/1963 | Kalopissis et al. | 132/7 |
| 3,148,126 | 9/1964 | Martin | 167/87.1 |
| 4,101,606 | 7/1978 | Cenci et al. | 260/857 UN |
| 4,727,111 | 2/1988 | Pettit, Jr. et al. | 525/190 |

OTHER PUBLICATIONS

Haefele et al. "Synthesis and Properties of Mercaptans, etc.", *Proc. Sci. Sect. Toilet Goods Assoc.*, No. 32, 52-9 (1959) in *Chem. Abst. 54:17233;-17234g (1960)*.
Voss, "Skin Sensitization by Mercaptans of Low Molecular Weight", *J. Invest. Derm.* 31, 373-9 (1958) in *Chem. Abst.* 53:20529e-f and *Chem. Abst. Sixth Coll. Ind. Formulas* A-C$_{12}$, C$_5$H$_{11}$NO$_2$S (1964).

*Primary Examiner*—Richard L. Raymond
*Assistant Examiner*—P. O'Sullivan

[57] ABSTRACT

Novel thiol-terminated hydroxyamides, and processes for their preparation and use are provided. These hydroxyamide compounds may be prepared by the reaction of a mercapto-functional alkyl ester, such as methylmercaptopropionate, with a molar excess of an alcohol-substituted amine, such as a $\beta$-hydroxyalkyl amine. The thiol-terminated hydroxyamides are useful as polymerization chain transfer agents, particularly when it is desirable to form polymers or oligomers containing functional hydroxyamide end groups. By chain terminating such polymers or oligomers with reactive hydroxyamide end groups the polymers or oligomers can be further reacted with acid-containing monomers or polymers to form block or graft copolymers.

2 Claims, No Drawings

THIOL-TERMINATED HYDROXYAMIDES

This application is a continuation of application Ser. No 392,491, filed Aug. 11, 1990, abandoned.

FIELD OF THE INVENTION

This invention is directed to a novel class of thiol-terminated hydroxyamide compounds useful as polymerization chain transfer agents. More particularly, the invention is directed to thiol-functional hydroxyamides, preferably thiol-functional β-hydroxyalkylamides, prepared by the reaction of a mercapto-functional alkylester with an alcohol-substituted amine. The thiol-functional hydroxyamide may be used to provide the resulting polymer or oligomer with a reactive hydroxyamide end group for subsequent preparation of block or graft copolymers.

BACKGROUND OF THE INVENTION

Polymers having carboxy or anhydride groups may be effectively cured or crosslinked by treating the polymer with a β-hydroxyalkylamide or a polymer containing β-hydroxyalkyamide functionality, as disclosed in U.S. Pat. Nos. 4,076,917; 4,101,606; 4,115,637; 4,138,541; 4,727,111 and 4,801,680. Examples of suitable acid or anhydride monomers which can be incorporated into the polymer backbone and crosslinked with β-hydroxyalkylamides include: unsaturated monocarboxylic acids; such as acrylic acid, methacrylic acid, crotonic acid and the like; unsaturated dicarboxylic acids such as maleic acid, 2-methylmaleic acid, itaconic acid, 2-methylitaconic acid, alpha,beta-methyleneglutaric acid and the like; unsaturated anhydrides such as maleic anhydride, itaconic anhydride, acrylic anhydride, methacrylic anhydride and the like; and amorphous carboxylic acid-group containing polyesters formed by the condensation reaction of aliphatic polyols and/or cycloaliphatic polyols with aliphatic and/or aromatic polycarboxylic acids and anhydrides.

The synthesis of β-hydroxyalkylamides and their use as crosslinkers, such as for example in the preparation of thermosetting coatings, was examined in: *B-Hydroxyalkylamides, Low Polluting Crosslinkers For Carboxyl Containing Polymers*, J. Lomax and G. Swift, Journal of Coatings Technology, Vol. 50, No. 643 (Aug. 1978) pages 49-55; *Esterification of N(2-Hydroxyalkyl)Amides*, Z. W. Wicks and N-C. Chiang, Journal of Coatings Technology, Vol. 54, No. 686 (Mar. 1982) pages 27-31; and *Reaction of N-(2-Hydroxyethyl)Amido Compounds*, Z. W. Wicks, M. R. Appelt and J. C. Soleim, Journal of Coatings Technology, Vol. 57, No. 726, (July 1985) pages 51-61.

None of these references, however, disclose or suggest thiol-terminated hydroxyamides or their use as chain transfer agents in polymerization reactions.

It was an object of the present invention to determine whether a thiol-terminated hydroxyamide, as for example a thiol-terminated β-hydroxyalkylamide, could be prepared and used as a chain transfer agent for the preparation of hydroxyamide-functional polymers or oligomers.

In addition, it is a further object of the invention to determine whether such hydroxyamide-containing polymers and oligomers could be subsequently reacted with acid-containing monomers or polymers to form block and graft copolymers.

For the purpose of the present disclosure the term "oligomer" shall refer to low molecular weight polymers which can function as monomers in subsequent polymerization reactions with other monomers or polymers. These functional oligomers are also referred to in the art as "macromers" or "macromonomers". The weight average molecular weight of these oligomers is typically in the range of from as low as about 300 to as high as about 5000.

SUMMARY OF THE INVENTION

Novel thiol-terminated hydroxyamide compounds, and particularly thiol-terminated β-hydroxyalkylamides, useful as polymerization chain transfer agents are provided. These compounds are prepared by the amidation of a mercapto-functional alkylester with a hydroxyamine, preferably using a molar excess of amine to ester. The thiol-containing hydroxyamides are also useful for preparing graft and block copolymers.

DETAILED DESCRIPTION OF THE INVENTION

The thiol-terminated hydroxyamide compounds of the invention are prepared by amidating a mercapto-functional alkylester with a hydroxyamine. The thiol-terminated hydroxyamide compounds of the invention may be represented by the structural formula I:

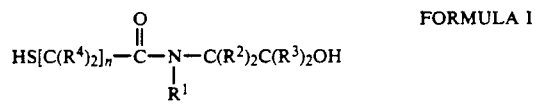

FORMULA I where $R^1$ is hydrogen, a lower alkyl having from 1 to 5 carbon atoms, or $HO(R^3)_2C(R^2)_2C-$;

where $R^2$, $R^3$ and $R^4$ are the same or different radicals selected from hydrogen, or straight or branched chain lower alkyl having from 1 to 5 carbon atoms, or where one of the R2 and one of the R3 radicals may be joined together with the carbon atoms; and where n is an integer equal to or greater than 1.

A preferred thiol-terminated hydroxyamide of the invention has the structural formula II:

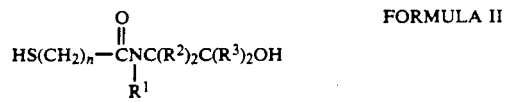

FORMULA II where $R^1$, $R^2$ and $R^3$, and n are as defined above, and where $R^4$ in Formula I is hydrogen.

The hydroxyamine is a compound having the structural formula III:

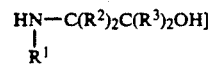

wherein $R^1$ is hydrogen, lower alkyl of from 1-5 carbon atoms, or $HO(R^3)_2C(R^2)_2C-$; $R^2$ and $R^3$ are the same or different radicals selected from hydrogen, straight or branched chain lower alkyl of from 1-5 carbon atoms or where one of the $R^2$ and one of the $R^3$ radicals may be joined together with the carbon atoms. Some representative amines of this type include 2-aminoethanol; 2-methylaminoethanol; 2-ethylaminoethanol; 2-n-propylaminoethanol; 2,2'-iminodiethanol; 2-aminopropanol; 2,2'-iminodiisopropanol; 2-aminocyclohexanol; 2-aminocyclopentanol; 2-aminomethyl-2-methylethanol; 2-n-butylaminoethanol; 2-methylamino-1,2-dimethylethanol; 2-amino-2-methyl-1-propanol; 2-amino-2-methyl-1,3-propanediol; 2-amino-2-ethyl-1,3-propanediol and 2-amino-2-hydroxymethyl-1,3-propanediol.

The mercapto-functional alkylesters which may be employed are those represented by the structural formula IV: $HS[C(R^x)_2]_nCOO(R)$; where R is methyl or any alkyl, straight or branched chain, preferably methyl; $R^x$ is hydrogen, methyl or a lower alkyl having 1 to 5 carbon atoms, and n is an integer, preferably 1 or 2. When $R^x$ is hydrogen and n is 2 the ester is alkyl mercaptopropionate, and when $R^x$ is hydrogen and n is 1 the ester is thioglycolate.

Increasing the n in the mercapto-functional alkylester, or preferably using a more hydrophobic $R^1$ in the hydroxyamine, increases the hydrophobicity of the resultant thiol-terminated hydroxyamide. This may be useful for achieving the desired degree of either water or organic solvent solubility which may be required.

When the mercapto-functional alkylester is thioglycolate the reaction is exothermic and can be conducted at room temperatures. When the n of the mercapto-functional alkylester is 2 or greater the reaction may be conducted at temperatures in the range of from about 25° Centigrade to about 120° Centigrade. In either case the reaction may be conducted in the absence of a catalyst. We found that while the time needed to complete the reaction decreased as the reaction temperature increased within this range, it was preferable to conduct the reaction at lower reaction temperatures to increase the yield of the desired product by avoiding or minimizing the formation of undesirable byproducts, such as for example those byproducts formed by condensation reactions.

In addition to using milder reaction temperatures, we found that in order to optimize the formation of the desired product a molar excess of hydroxyamine to mercapto-functional ester is preferred. We found that if less than one equivalent of amine per equivalent of thiol is used the product yield drops dramatically (below 50%) and the presence of higher molecular weight byproducts increase. We have found that it is preferred to utilize a molar excess of amine to thiol of from about 2/1 to about 3/1 and reaction temperatures in the range of from about 60° to about 80° C. (when the n of the mercapto-functional alkylester is greater than 1) to obtain a yield of product in the range of from about 70 to about 75%, and more preferably, in such instances, to utilize a molar excess of 2/1 at a temperature of 80° C.

Removal of unreacted amines and condensation byproducts can be employed to increase product purity. We have found a preference for purification of the reaction product by extraction using an organic solvent, such as for example methylene chloride, rather than by vacuum distillation.

The thiol-terminated hydroxyamide is useful as a polymerization chain transfer agent for any type of free radical initiated polymerization. The ability to terminate any free radical initiated polymer, whether prepared in water or an organic solvent, with a reactive end group may provide advantages during subsequent processing or use of the polymer so terminated over the same polymer terminated with a non reactive, conventional polymerization chain transfer agent. We have found that the thiol-terminated hydroxyamides of the invention can be employed as a chain transfer agent to prepare polymers and oligomers having weight average molecular weights as low as about 300 weight average molecular weight. In addition, the thiol-terminated hydroxyamide may be useful in chain terminating higher molecular weight polymers having weight average molecular weights on the order of 100,00 or higher. The thiol-terminated hydroxyamide is used to terminate polymerization reactions in the same manner as conventional chain transfer agents known in the art, such as for example n-dodecyl mercaptan, at the same concentrations as such conventional chain transfer agents are commonly employed, and with no special processing requirements.

By placing a hydroxy amide functional group at the end of the polymer chain the polymer produced will possess ther ability to more effectively react with acid-containing polymers. This may be particularly advantageous for the preparation of thermosetting coating compositions, such as for example in acrylic or polyester powder coatings, such as, for example, to permit the coating to be formulated with a lower concentration of crosslinker to achieve the same crosslink density.

The thiol-terminated hydroxyamide is useful in the preparation of reactive oligomers. The hydroxyamide end group can be reacted with any carboxylic acid-containing compound, including carboxylic acid containing polymerizable monomers. This may be accomplished by mixing the thiol-terminated hydroxyamide with the carboxylic acid containing compound and heating the mixture to a temperature of from about 100 degrees Centigrade to about 160 degrees Centigrade, preferably from about 110 degrees to about 130 degrees Centigrade. In the case where the carboxylic acid containing compound is a polymerizable monomer, the resulting macromer may then be copolymerized using conventional free radical initiation polymerization conditions with one or more copolymerizable monomers to incorporate the macromer into the polymer backbone as pendant graft segments.

The following examples illustrate the preparation and use of the thiol-terminated hydroxyamides of the invention. These examples are illustrative only and are not intended to limit, and should not be construed as limiting, the scope of the invention as other methods for preparing and using the thiol-terminated hydroxyamides of the invention should be obvious to those of ordinary skill in the art from the description provided herein.

EXAMPLE 1

Preparation of Thiol-terminated Hydroxyamide

To a 500 milliliter flask was added 1 mole (117 grams) of N-butyl-N-hydroxyethylamine. The flask was cooled by placing it in an ice bath. One half mole (53 grams) of methyl thioglycolate was then added dropwise over one hour to the flask while the temperature of the flask contents was maintained at about 45° C. The flask was then allowed to warm to room temperature over 5 hours. The contents of the flask were transferred to a separatory funnel. The flask was rinsed with 200 milliliters of methylene chloride and the rinses were added to the separatory funnel. The transferred materials were then washed with three portions (150 ml) of 5% sodium hydroxide. This served to form the thiolate anion and resulted in the extraction of the thiol into the aqueous phase. The combined basic, aqueous extracts were washed with two 50 milliliter portions of methylene chloride to remove all non-aqueous base soluble contaminants such as higher molecular weight condensation byproducts. The methylene chloride washes were discarded. The aqueous base solution was then acidified with 6N hydrochloric acid to pH 1. This served to protonate the thiolate anion thereby reducing its water solubility and allowing its extraction into methylene chloride. The acidified aqueous phase was washed three times with 150 ml portions of methylene chloride and the combined extracts were dried by slurrying with 10 grams of anhydrous magnesium sulfate. The magnesium sulfate was removed by filtration though a glass wool plug and the methylene chloride was stripped on a Buchi rotary evaporator at 35 degrees C. at 20 mm Hg. The resulting product, N-butyl-N-hydroxyethyl mercaptoacetamide (63 grams, 0.36 moles, 72% yield) was analyzed by NMR (Bruker AM-250 mHz). Silver nitrate titration showed 5.65 meq thiol/gram (theory 5.71 meq thiol/gram).

EXAMPLE 2

Preparation of N-butyl-N-hydroxyethyl-3-mercaptopropionate

To a 500 milliliter flask was added 100 grams (0.832 grams) of methyl mercaptopropionate and 195 grams (1.66 moles) of N-butylhydroxyethylamine. The reaction mixture was heated to 80 degrees Centigrade for 8 hours and then was allowed to cool to room temperature. The product, N-butyl-N-hydroxyethyl-3-mercaptopropionate, was purified as set forth in example 1. The yield of product was 70%.

EXAMPLE 3

Preparation of a hydroxyethylamide-terminated polymethyl methacrylate oligomer of molecular weight of about 2000

To a well stirred, nitrogen flushed, flask containing 100 grams of toluene maintained at 80 degrees Centigrade was added, dropwise over 2.5 hours, in three separate feeds: (1) 300 grams of methyl methacrylate(2.99 moles) in 150 grams toluene; (2) 28.5 grams (0.149 moles) of N-butyl-N- hydroxyethyl mercaptoacetamide; and (3) 1.5 grams of 2,2-azobis-(2-methylbutyronitrile) in 10 grams of toluene as initiator. After the feeds were complete the reaction mixture was maintained at 85 degrees Centigrade for an additional hour and then was allowed to cool to room temperature. Conversion to polymer was found to be 95%.

EXAMPLE 4

Methacrylate Functionalization of the B-hydroxyethylamide-terminated polymethyl methacrylate oligomer The polymethyl methacrylate oligomer of example 3 (330 grams, 0.149 moles) in toluene was heated to reflux with 14.1 grams (0.164 moles) of methacrylic acid along with 0.1 grams of methoxy hydroquinone as inhibitor. After 6 hours at reflux, titration of an aliquot of the reaction mixture indicated consumption of greater than 95% of the theoretical methacrylic acid. NMR analysis confirmed that almost quantitative conversion to the macromer.

EXAMPLE 5

Preparation of graft copolymers: Polybutyl acrylate with pendant methacrylate chains (A) A toluene solution of a polybutyl acrylate polymer (500 grams) containing 5% methacrylic acid was heated to reflux with 200 grams of B-hydroxyethylamide-terminated polymethyl methacrylate oligomer-(Example 3). After 8 hours acid-base titration of an aliquot indicated nearly complete esterification of the polymethyl methacrylate oligomer into the polybutyl acrylate backbone.

(B) To a well stirred flask containing 100 grams of toluene at 85 degrees Centigrade was added dropwise over 2.5 hours a solution of the methacrylate functional polymethyl methacrylate oligomer of example 4 (100 grams), butyl acrylate (240 grams) and methacrylic acid (10 grams). A solution of 2.5 grams of azobis-2-methylbutyronitrile in 10 grams of toluene was simultaneously fed to the reaction mixture to initiate polymerization. The reaction mixture was maintained at 85 degrees Centigrade for an additional hour and then allowed to cool to room temperature. The product was analyzed by NMR (Bruker AM-250 mHz) and by gel permeation chromatography. Both analyses demonstrated essentially complete incorporation of the polymethyl methacrylate oligomer (Example 4) into the polybutyl acrylate backbone.

What is claimed is:

1. A method of using a thiol-terminated hydroxyamide of the structural formula:

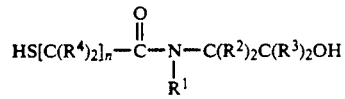

where $R^1$ is hydrogen, a lower alkyl having from 1 to 5 carbon atoms, or $HO(R^3)_2C(R^2)_2C-$;

$R^4$ are the same or different radicals selected from hydrogen, or straight or branched chain lower alkyl having from 1 to 5 carbon atoms, or where one of the $R^2$ and one of the $R^3$ radicals located on adjacent carbon atoms may be joined together with said adjacent carbon atoms; and where n is an integer greater than or equal to 1, as a chain transfer agent in a free radical initiated polymerization reaction.

2. A method of forming a reactive oligomer comprising reacting a carboxylic acid-containing monomer or oligomer with a thiol-terminated hydroxyamide of structural formula:

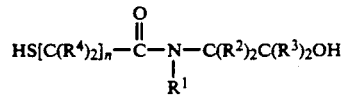

where $R^1$ is hydrogen, a lower alkyl having from 1 to 5 carbon atoms, or $HO(R^3)_2C(R^2)_2C-$;

where $R^2$, $R^3$ and $R^4$ are the same or different radicals selected from hydrogen, or straight or branched chain lower alkyl having from 1 to 5 carbon atoms, or where one of the $R^2$ and one of the $R^3$ radicals located on adjacent carbon atoms may be joined together with said adjacent carbon atoms; and where n is an integer greater than or equal to 1, under free radical initiated polymerization conditions.

* * * * *